(12) United States Patent
Mosel et al.

(10) Patent No.: US 6,416,504 B2
(45) Date of Patent: Jul. 9, 2002

(54) URETHRAL CATHETER HOLDER

(75) Inventors: Brian J. Mosel, Dublin; Loren L. Roy, San Jose; John P. Claude, San Carlos; Frank W. Ingle, Palo Alto, all of CA (US)

(73) Assignee: SURx, Inc., Livermore, CA (US)

( * ) Notice: Subject to any disclaimer, the term of this patent is extended or adjusted under 35 U.S.C. 154(b) by 0 days.

(21) Appl. No.: 09/288,865

(22) Filed: Apr. 9, 1999

Related U.S. Application Data

(60) Provisional application No. 60/104,818, filed on Oct. 19, 1998.

(51) Int. Cl.[7] .................. A61M 25/01; A61M 25/02; A61M 25/04; A61M 25/06; A61M 25/08
(52) U.S. Cl. .................. 604/528; 600/587; 600/591; 600/202; 606/1; 604/264
(58) Field of Search .................. 604/599.04, 174, 604/179, 540, 544, 93.01, 95.02, 96.01, 100.03, 103.05, 349, 505, 264, 528; 600/591, 561, 546, 566, 587, 202

(56) References Cited

U.S. PATENT DOCUMENTS

| | | | |
|---|---|---|---|
| 4,089,337 A | * 5/1978 | Kronner | 128/348 |
| 4,233,991 A | * 11/1980 | Bradley et al. | 128/733 |
| 4,484,585 A | * 11/1984 | Baier | 128/748 |
| 4,652,259 A | * 3/1987 | O'Neill | 604/54 |
| 4,710,169 A | * 12/1987 | Christopher | 604/104 |
| 4,825,875 A | * 5/1989 | Ninan et al. | 128/748 |
| 5,318,541 A | * 6/1994 | Viera et al. | 604/159 |
| 5,334,159 A | 8/1994 | Turkel | |
| 5,389,100 A | 2/1995 | Bacich et al. | |
| 5,433,216 A | * 7/1995 | Sugrue et al. | 128/778 |
| 5,460,606 A | * 10/1995 | Daneshvar | 604/96 |
| 5,566,680 A | 10/1996 | Urion et al. | |
| 5,653,705 A | 8/1997 | De La Torre et al. | |
| 5,690,645 A | * 11/1997 | Van Erp et al. | 606/108 |
| 5,891,457 A | * 4/1999 | Neuwirth | 424/430 |
| 5,964,732 A | * 10/1999 | Willard | 604/117 |

OTHER PUBLICATIONS

Kim et al., "The vesico–urethal pressuregram analysis of urethal function under stress" J. Biomechanics 30(1):19–25, 1997.*

* cited by examiner

*Primary Examiner*—Glenn K. Dawson
*Assistant Examiner*—Jennifer Maynard
(74) *Attorney, Agent, or Firm*—Townsend Townsend Crew LLP; Mark D. Barrish, Esq.

(57) ABSTRACT

A urethral catheter holder (10), comprising a supporting base (20); a suspension housing (22) mounted to supporting base (20); a catheter securement device (24) adapted to hold a catheter (30) passing longitudinally therethrough, catheter securement device (24) being adapted to slide longitudinally within suspension housing (22); and a biasing device (26) adapted to push a catheter guide (28) of catheter securement device (24) into engagement with the patient's external meatus (EM).

11 Claims, 10 Drawing Sheets

URETHRAL CATHETER HOLDER

This application claims the benefit and priority of U.S. patent application Ser. No. 60/104,818, filed Oct. 19, 1998, the full disclosure of which is hereby incorporated by reference for all purposes.

TECHNICAL FIELD

The present invention relates to catheter based pressure sensing systems for diagnosing female urinary incontinence, and in particular to systems for determining the relationship between urethral pressure and vesicle pressure in response to changes in abdominal pressure. Preferred aspects of the present invention relate to urethral catheter holder mechanisms.

BACKGROUND OF THE INVENTION

Female urinary incontinence can be evaluated by determining the relationship between a patient's urethral pressure and her vesicle (ie: bladder) pressure. Specifically, incontinence will occur when her vesicle pressure exceeds her urethral pressure. A continence margin can thus be defined by the difference between the patient's urethral pressure and the vesicle pressure.

Both urethral pressure and vesicle pressure will change in response to changes in abdominal pressure, however, the urethral and vesicle pressures may change at different rates as the abdominal pressure changes. Accordingly, incontinence may occur at various abdominal pressures at which the vesicle pressure exceeds the urethral pressure. Incontinence can therefore be evaluated by producing a pressuregram showing the relationship between the urethral pressure and the vesicle pressure of the patient at different abdominal pressures.

Measuring the patient's vesicular and urethral pressures with a pressure sensing catheter can be accomplished by moving a pressure sensor on the catheter from the patient's bladder, (at which the vesicle pressure is measured), through the patient's urethra (at which maximum urethral pressure is measured). Specifically, a urinary catheter with internal or external pressure transducers can be used to take pressure measurements at the proximal urethra, mid-urethra, and distal urethra. Typically, such a pressure sensing catheter is first introduced through the urethra into the bladder. The pressure sensing catheter is then withdrawn through the urethra with pressure measurements taken at the proximal urethra (being 5–10 mm from the urethro-vesicular junction), the mid-urethra (being the point of maximum resting urethral pressure) and the distal urethra, (being 5–10 mm from the external meatus).

The measurements of the patient's vesicular and urethral pressures are preferably taken at various abdominal pressures. Such different abdominal pressures can conveniently be generated simply by having the patient cough with different amounts of effort. For example, a mild couch would generate a minimal increase in abdominal pressure, whereas a more intense cough will generate a greater abdominal pressure. The increase in abdominal pressure will cause both the urethral and vesicle pressures to increase.

Unfortunately, such coughing will also tend to cause movement of the patient's bladder and urethra. As such, it is difficult to maintain the position of the pressure sensing catheter relative to the urethra during the jarring movement of the urethra caused by the patient coughing. Unwanted movement of the catheter relative to the urethra caused by the jarring action of the patient coughing tends to compromise the accuracy of the pressure measurements.

It is important, therefore, to maintain the catheter at each of the desired measurement positions in the urethra when taking the pressure measurements. To date, an effective solution for maintaining the position of the pressure sensing catheter at preferred locations along the urethra when the urethra moves in response to the patient's cough have not been found.

SUMMARY OF THE INVENTION

The present invention provides a female urethral catheter holder which is adapted to support a pressure sensing catheter such that the catheter can be positioned at various desired locations along the patient's urethra, allowing for the catheter to move in response to urethral movement, such that a pressure sensing transducer disposed on the catheter does not move relative to the urethra when the patient coughs.

In a preferred aspect of the present invention, the urethral catheter holder comprises a supporting base, which is adapted to register against the labia of the patient; a suspension housing mounted to the supporting base; a catheter securement device, (which is adapted to move within the suspension housing when the patient coughs such that the catheter moves with the urethra); and a biasing device. In preferred aspects, the catheter securement device comprises a catheter guide which is adapted to contact against the external meatus of the patient's urethra. The biasing device operates to provide a pre-loading force on the catheter guide, thereby holding the catheter guide against the external meatus of the patient's urethra such that the catheter securement device moves with the movement of the urethra. Additionally, the biasing device operates to push the catheter securement device against the supporting base, thereby minimizing unwanted motion of the catheter securement device within the suspension housing.

The catheter securement device is adapted to support the catheter in a manner such that the catheter moves in response to movement of the urethra, with the catheter remaining in generally the same position relative to the surrounding urethra when the patient coughs. In a preferred aspect, the catheter securement device comprises a torroidal balloon, a generally ring-shaped balloon support mount surrounding the torroidal balloon and a pneumatic or hydraulic pressure tube for inflating or deflating the torroidal balloon. The catheter passes longitudinally through the catheter holder and is received through the orifice defined by the torroidal balloon. Inflation of the torroidal balloon will cause it to expand radially inwardly such that it's central orifice contracts, thereby gently pushing against the sides of the catheter.

In other preferred aspects of the invention, the catheter securement device comprises a mechanical clamp which is mounted to move longitudinally within the suspension housing.

Optionally, the present urethral catheter holder may also comprise a pair of leg straps, which can be wrapped around the patient's thighs, (or a stretchable undergarment with leg straps attachable thereto), such that the supporting base of the catheter holder can be held at a generally fixed position against the labia of the patient. An advantage of such leg straps is that pressure measurements can then be taken easily with the patient in different positions, including supine and sitting. An additional advantage of the present system is that it allows hands-free operation for the clinician.

DETAILED DESCRIPTION OF THE PREFERRED EMBODIMENT

Figure 1:
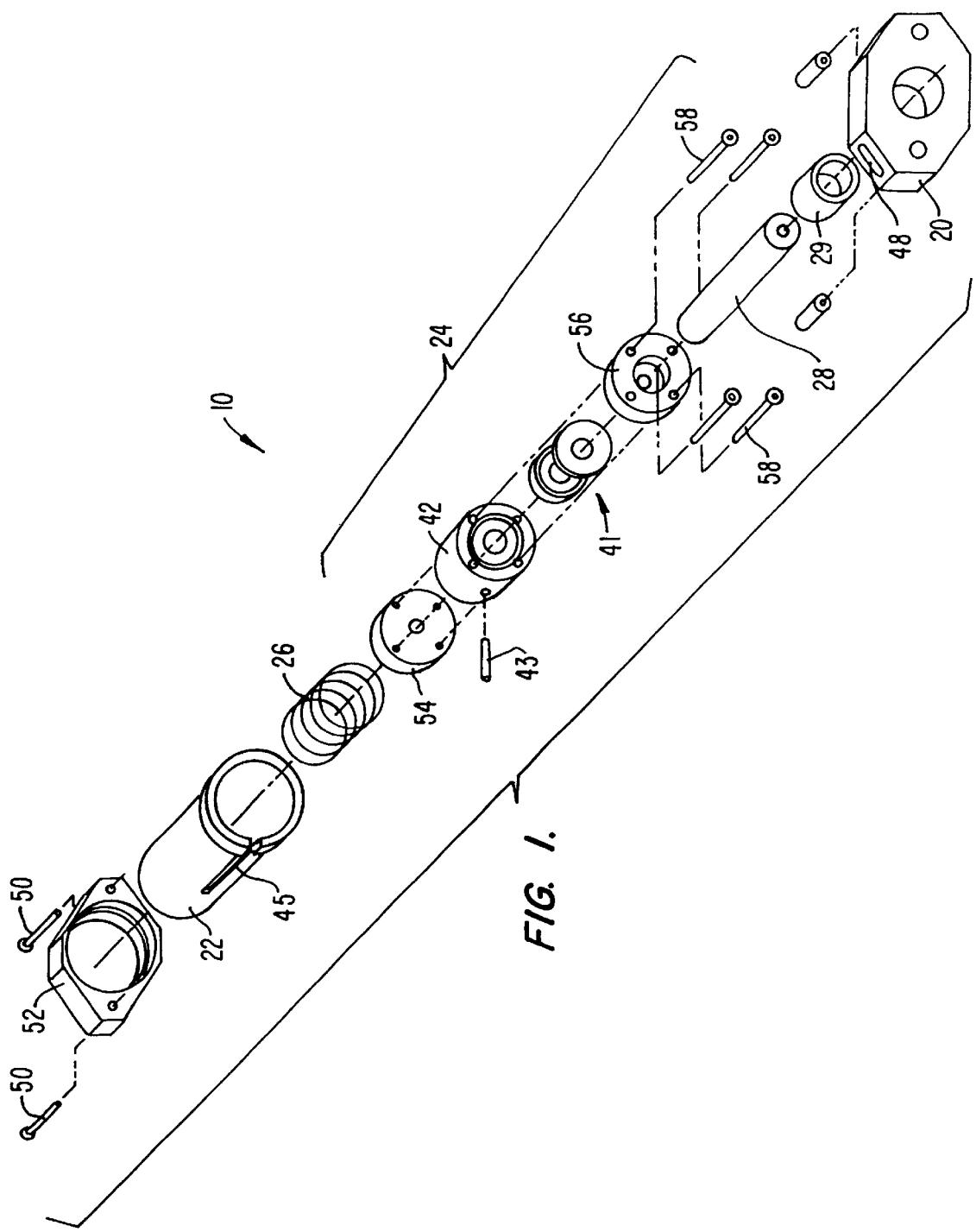
FIG. 1 is an exploded view of the urethral catheter holder.
Figure 2:
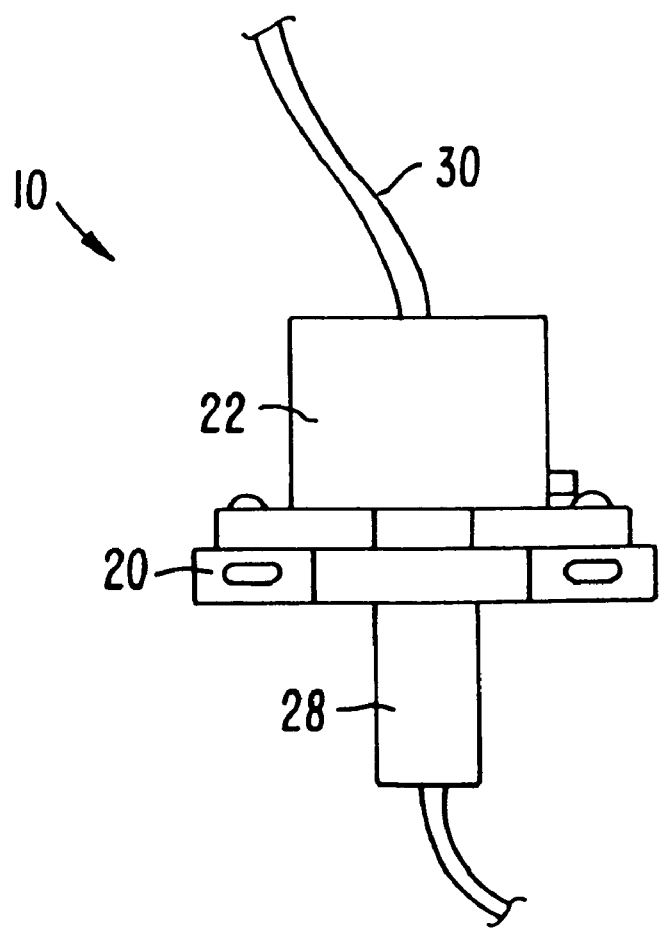
FIG. 2 is a top view of the urethral catheter holder.
Figure 3:
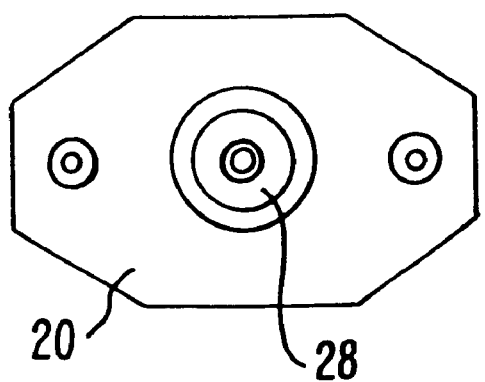
FIG. 3 is a front view of the urethral catheter holder.

In preferred aspects of the present invention, a urethral catheter holder is provided. FIG. 1 shows an exploded view of the assembly of urethra catheter holder 10, comprising a supporting base 20, a suspension housing 22, a catheter securement device 24, a biasing element 26, and a catheter guide 28. Assembled views of catheter holder 10 are shown in FIGS. 2, 3, 4, and 5. As shown in FIG. 2, a catheter 30 is received longitudinally through catheter holder 10, as shown.

Catheter holder 10 is adapted to hold catheter 30 such that supporting base 20 can remain in contact with the patient's labia while catheter 30 moves longitudinally in response to movement of the patient's urethra when the patient coughs. Accordingly, one advantage of the present invention is that catheter 30 can be positioned to remain in at the same relative location with respect to the patient's urethra when the patient coughs. The ability of catheter securement device 24 to hold catheter 30 to allow for catheter movement in response to urethra movement, without tightly pinching catheter 30 is accomplished by the present novel catheter securement system, as follows.

Figure 6:
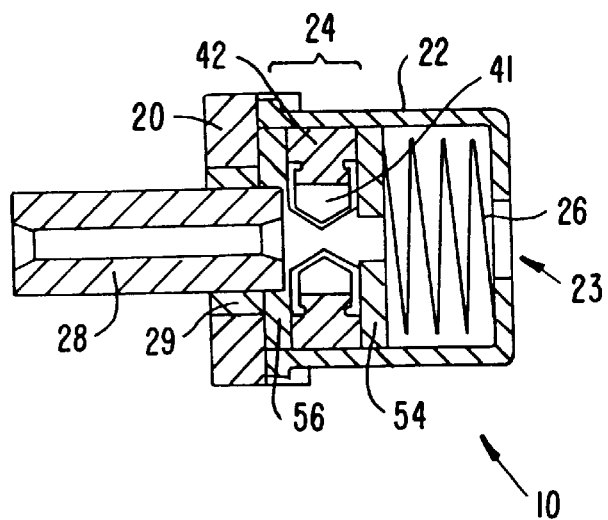
FIG. 6 is a sectional plan view of the urethral catheter holder taken along line 6—6 in FIG. 5.
Figure 7A:
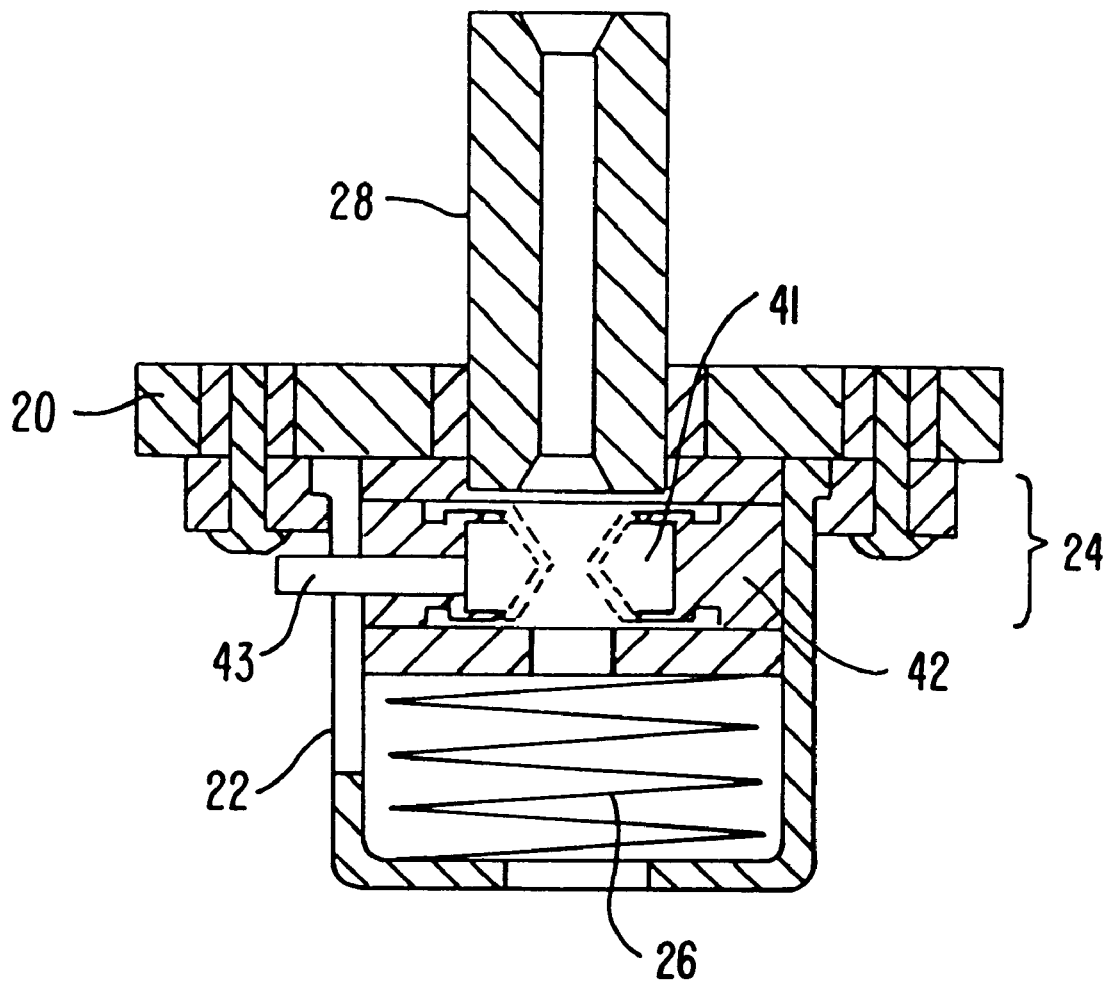
FIG. 7A is a sectional elevation view of the urethral catheter holder taken along line 7-6 in FIG. 5.

Referring to FIGS. 6 and 7A, catheter securement device 24 preferably comprises a torroidal balloon 41, a generally ring-shaped balloon support mount 42, a pneumatic or hydraulic pressure tube 43, and a catheter guide 28, as shown. Together, torroidal balloon 41, balloon support 42, pressure tube 43, and catheter guide 28 are adapted to slide longitudinally as a unit within the suspension housing 22. A bushing 29, which may be made of Teflon, is provided to enable catheter guide 28 to slide freely through supporting base 20. Biasing element 26, which may preferably comprise a mechanical spring, provides a pre-loading force which gently pushes catheter guide 28 against the external meatus EM of the patient's urethra 50, (see FIG. 10). Accordingly, catheter guide 28 will move together with the patient's urethra such that catheter guide 28 identically tracks the movement of urethra 50.

Figure 7B:
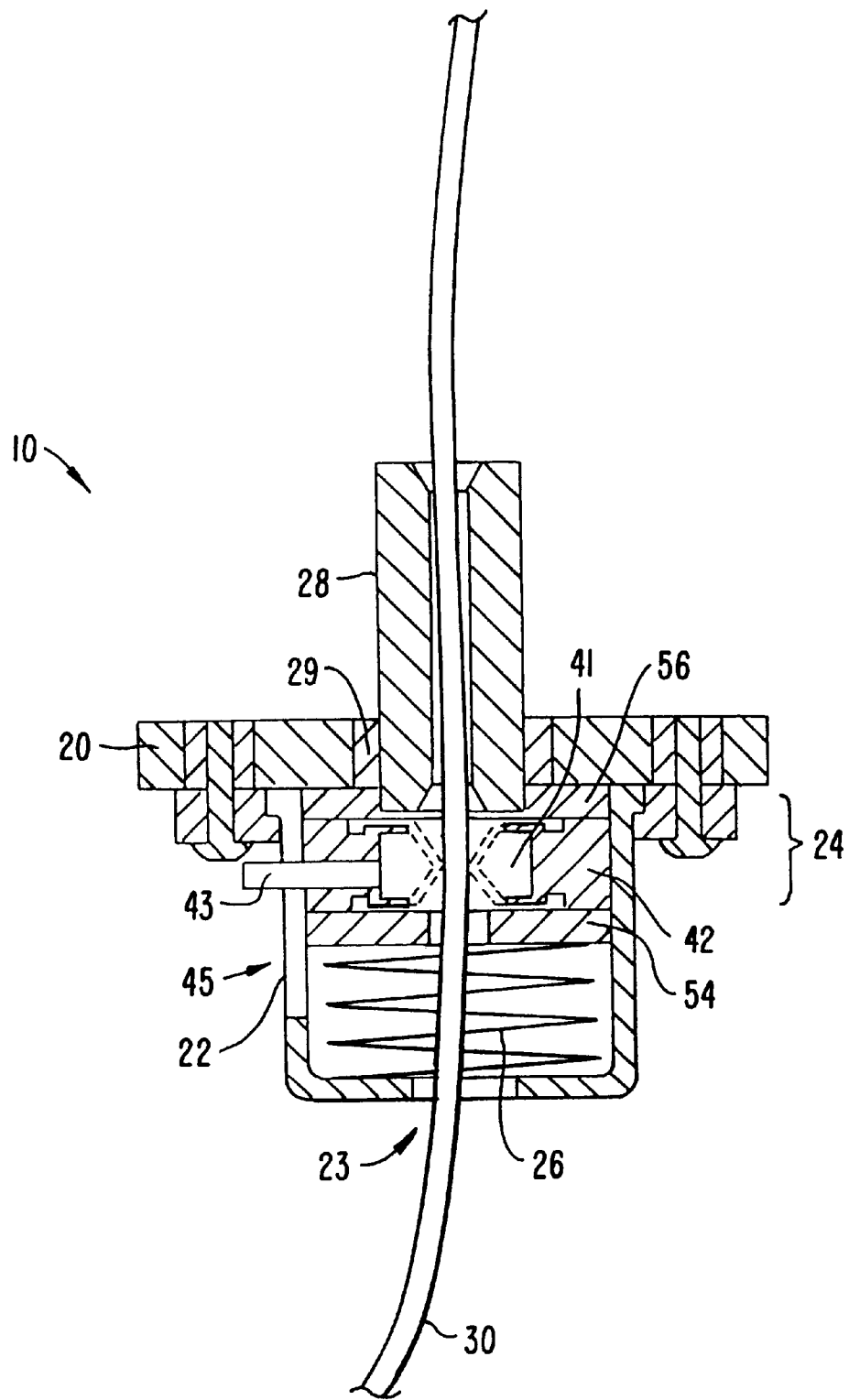
FIG. 7B is a view corresponding to FIG. 7A, but with a catheter received therethrough.

As shown in FIG. 7B, catheter 30 is preferably received through an opening 23 in suspension housing 22 and passes longitudinally through catheter holder 10, as shown. Torroidal balloon 41 is inflated by way of pressure tube 43, which can be connected a pneumatic or a hydraulic pressure system (not shown). As torroidal balloon 41 is inflated, its center orifice will tend to close as the innermost sides of balloon 41 expand inwardly, thereby gently pushing radially inwardly upon the side of catheter 30 around its circumference, thus holding catheter 30 in a fixed position relative to balloon 41.

Figure 4:
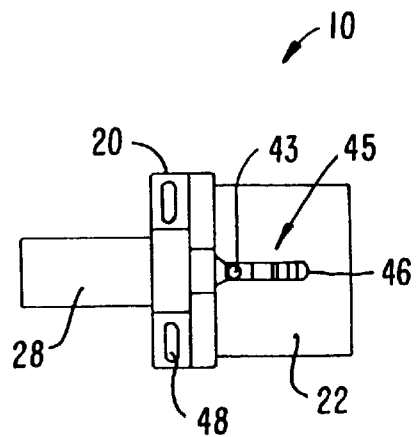
FIG. 4 is a right-side view of the urethral catheter holder.
Figure 5:
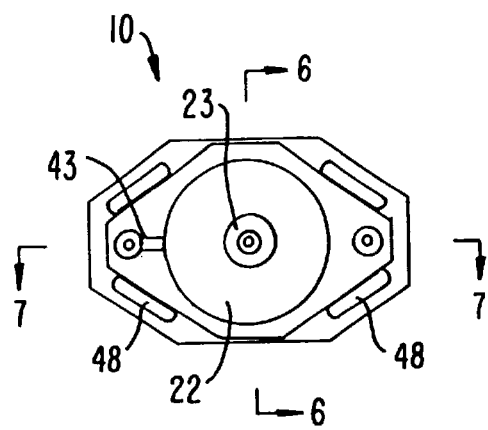
FIG. 5 is a rear view of the urethral catheter holder.

Catheter securement device 24, (comprising torroidal balloon 41, support mount 42, pressure tube 43, and catheter guide 28), is adapted to slide longitudinally within suspension housing 22. As can be seen in FIGS. 1 and 4, a groove 45 running longitudinally through suspension housing 22 provides freedom of longitudinal movement for pressure tube 43, which passes therethrough, as shown.

In preferred aspects of the invention, torroidal balloon 41 is made of silicon rubber, and support housing 22 and catheter guide 28 are made either of aluminum, or a polycarbonate material. It is to be understood, however, that support housing 22 and catheter guide 28 can be made of any suitable bio-compatible material.

Further structural details of the present invention are seen in the exploded view of FIG. 1. A pair of fasteners 50 can be used to secure housing flange 52 to supporting base 20. Backing plates 54 and 56 can also be provided on opposite sides of catheter securement device 24. Backing plates 54 and 56 may preferably be made of aluminum. Fasteners 58 can be provided for securing backing plates 54 and 56 to catheter securement device 24.

Figure 12:
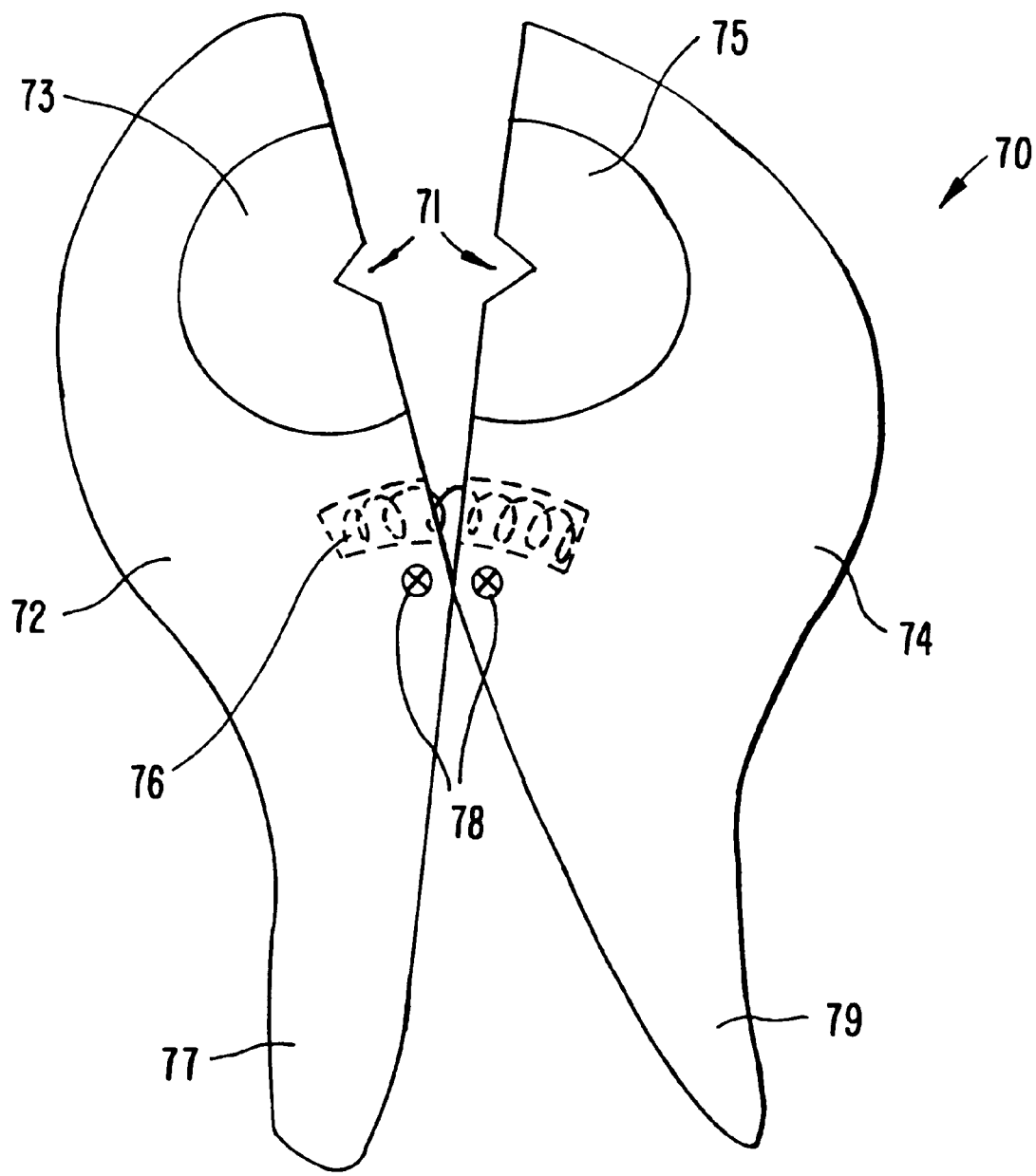
FIG. 12 shows a mechanical clamp for use in the catheter securement device.
Figure 13:
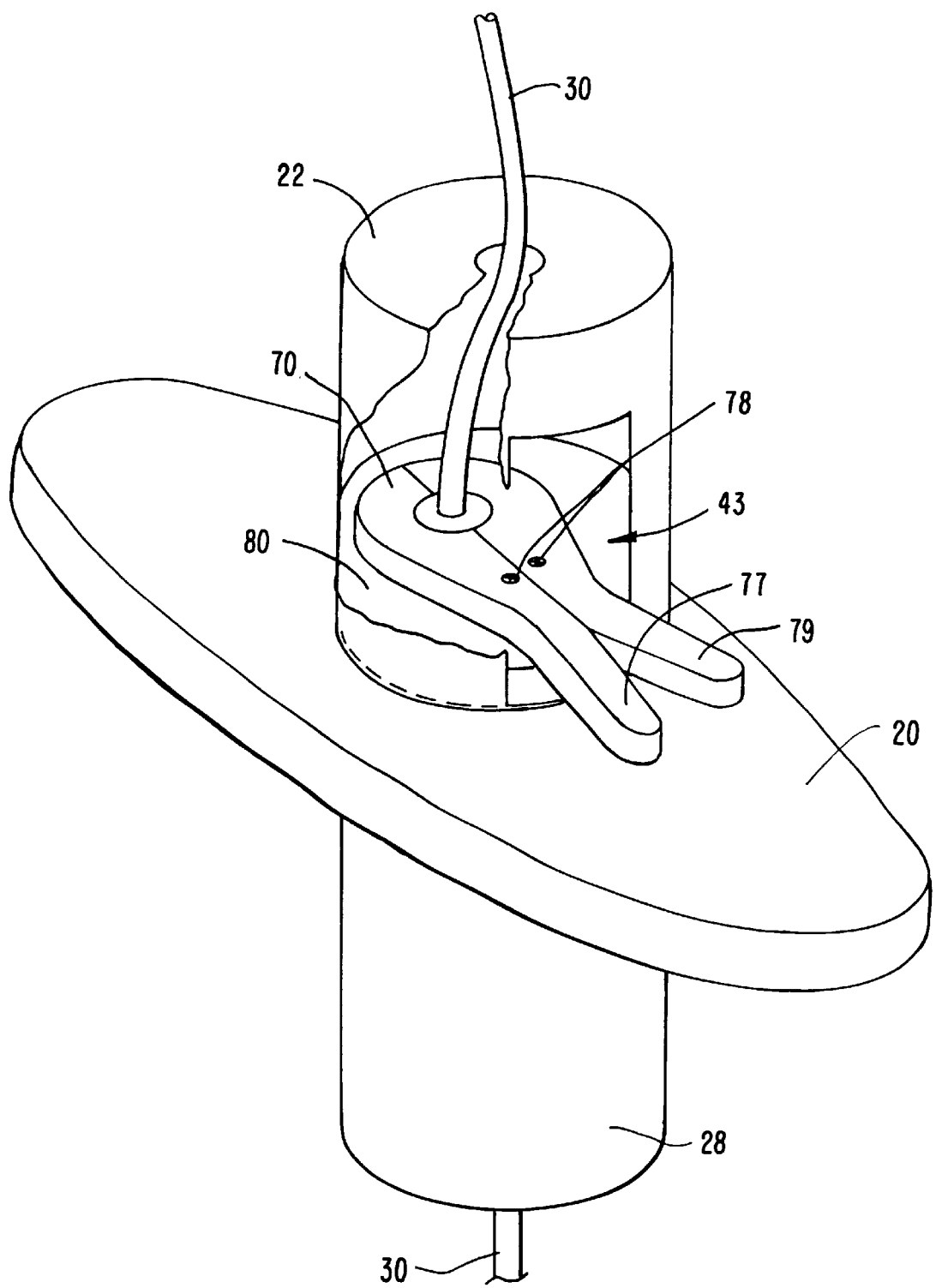
FIG. 13 shows a perspective view of an alternate embodiment of the present invention, comprising the mechanical clamp of FIG. 12.

An alternate embodiment of the catheter securement device is shown in FIGS. 12 and 13. The system shown in FIGS. 12 and 13 operates similar to catheter system 24, moving to track movement of the patient's urethra, as explained herein. Instead of requiring a torroidal balloon and balloon support mount, a mechanical clamping system which moves longitudinally is response to urethral movement is provided.

Referring to FIG. 12, a mechanical clamp 70 is provided. Clamp 70 comprises a pair of hard opposite portions 72 and 74 supporting soft inner surfaces 73 and 75 which may be manufactured of silicone or medical tubing. A notch 71 is provided for supporting a catheter therein as illustrated in FIG. 13. A spring 76 will bias hard opposite portions 72 and 74 together, closing clamp 70 around a catheter received therein. As seen in FIG. 13, clamp 70 can be mounted to a backing 80, wherein backing 80 moves longitudinally in suspension housing 22 under the influence of a biasing element, (functioning in the manner of biasing element 26 as herein described). As can be seen, levers 77 and 79 project out through groove 43. Pinching on levers 77 and 79 causes opposite portions 72 and 74 to separate, such that catheter 30 can be received therein. Levers 77 and 79 move longitudinally in groove 43 when catheter groove 28 and backing 80 move in response to movement of the patient's urethra. Clamp 70 may be secured to backing 80 by a pair of pins 78. It is to be understood that other mechanical clamping systems are possible, all keeping within the scope of the present invention, including the use of both expansion and compression springs to cause the mechanical clamp to securely hold the catheter in position.

Figure 8:
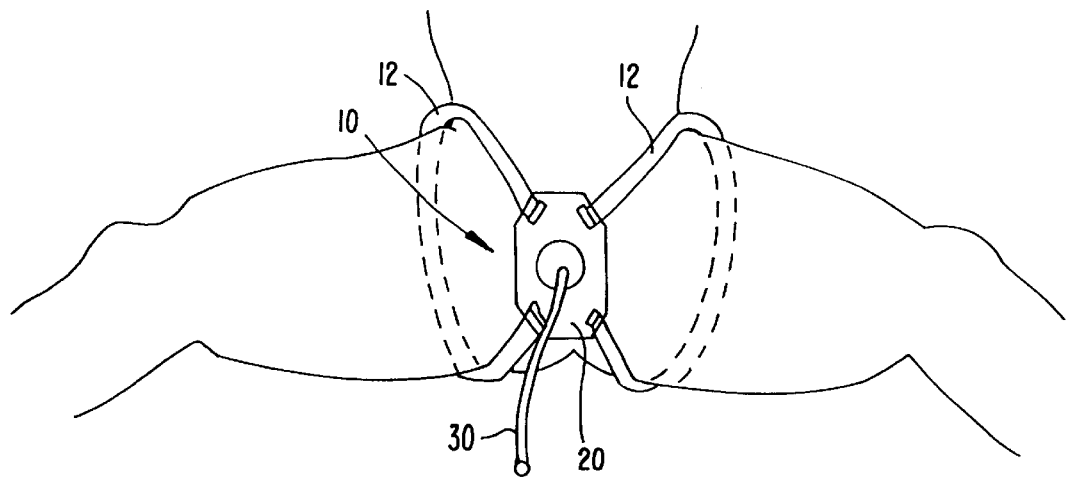
FIG. 8 shows positioning of the catheter holder by way of leg straps.
Figure 9:
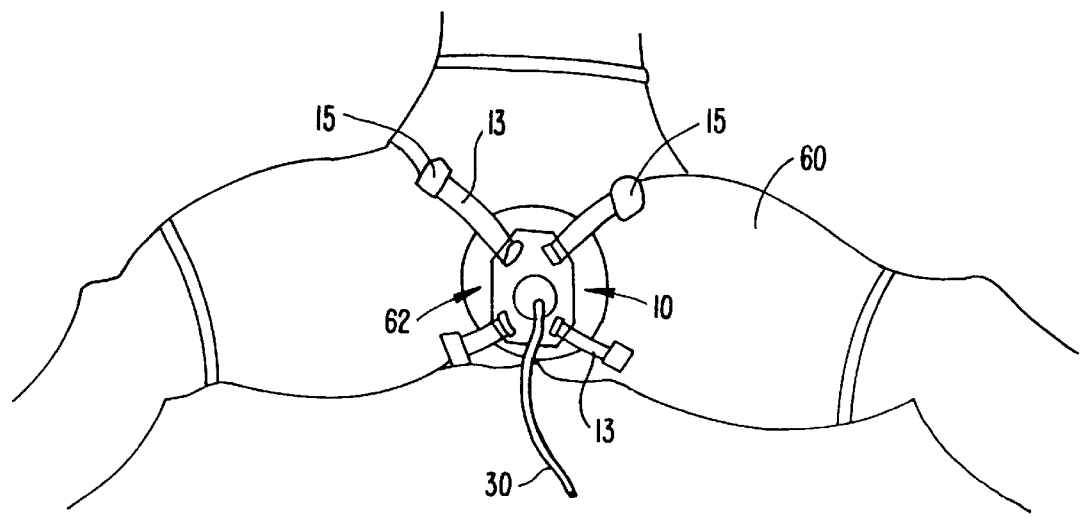
FIG. 9 shows positioning of the catheter holder by way of leg straps and a stretchable undergarment.

In a preferred aspect of the invention, optional leg straps are provided for registering the supporting base 20 of catheter holder 10 against the labia of the patient as catheter guide 28 moves with the urethra. Referring to FIG. 8, catheter holder 10 can be held in position with two leg straps 12 connected at opposite ends to supporting base 20, as shown. Alternatively, as shown in FIG. 9, a stretchable undergarment 60 can be worn by the patient. Undergarment 60 has an opening 62 over which catheter holder 10 can be fastened in position by way of four leg straps 13, wherein each of leg straps 13 have a Velcro-type patch 15 at their ends as shown for connecting fastening leg straps 13 directly to stretchable undergarment 60. Leg straps 12 may themselves be secured to slots 48 in supporting base 20 either by hooks (not shown) or by passing an end of each leg strap 12 through slot 60 and then folding the leg strap over upon itself and securing it into position with a Velcro-type fastener.

Figure 10:
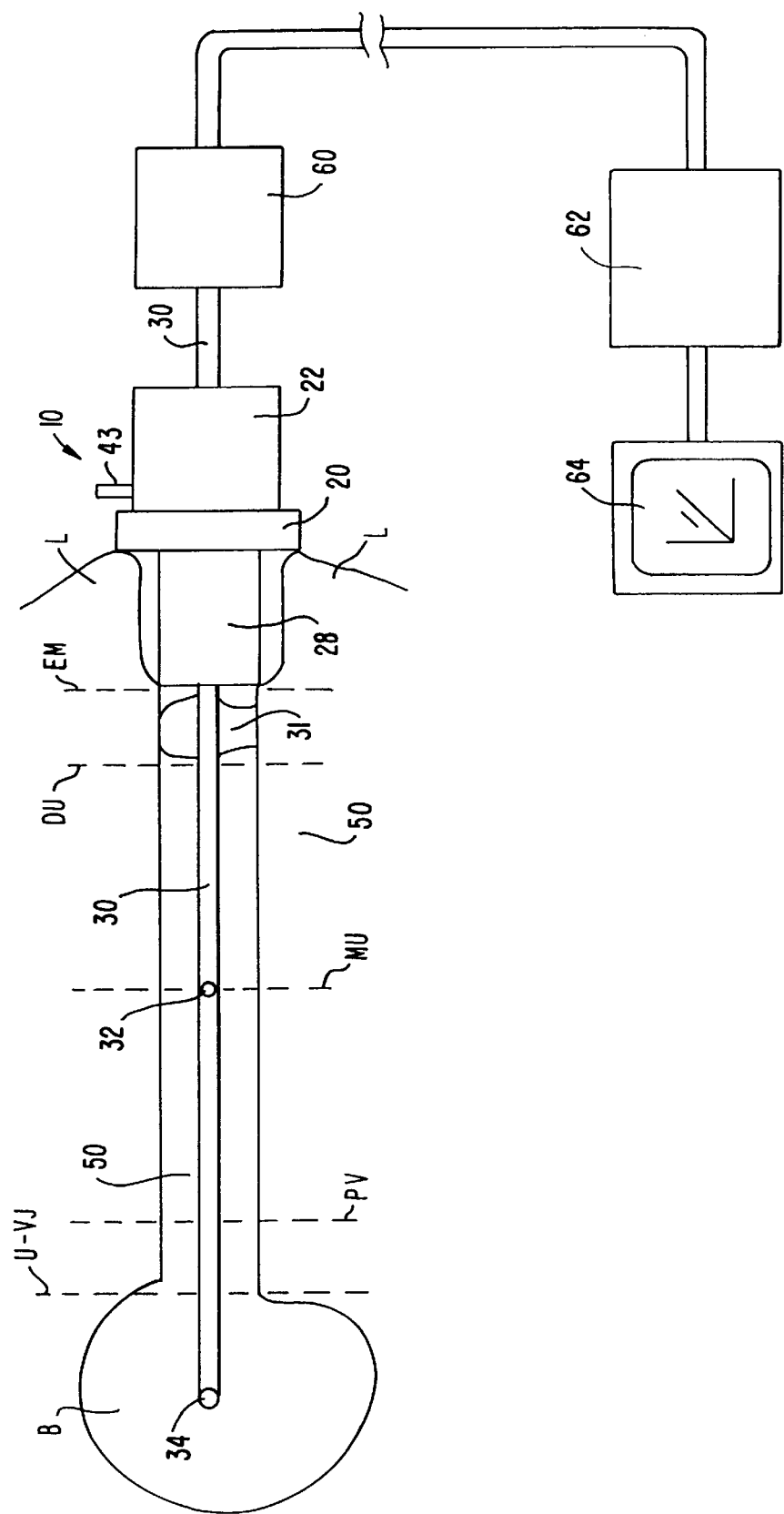
FIG. 10 is a schematic view of a system for evaluating female urinary incontinence incorporating the present urethral catheter holder.

In another aspect of the present invention, a system for evaluating female urinary incontinence is provided. Preferably, the system for evaluating female urinary incontinence comprises the present urethral catheter system as above described. Referring to FIG. 10, catheter 30 has pressure sensors 32 and 34 disposed thereon, as shown. Catheter 30 is preferably inserted through urethra 50 into bladder B. Catheter 30 is then controllably retracted through urethra 50 by a mechanical retractor 60. Accordingly, pressure sensors 32 and 34 can be positioned to take pressure measurements at each of the proximal urethra PU (which is located approximately 5–10 mm from the urethro-vesicular junction U-VJ), the mid-urethra MU, (where the vesicle pressure is greatest), to the distal urethra (which is located approximately 5–10 mm from the external meatus EM). It is to be understood that the present invention can operate with one or more pressure sensors 32 and 34 since catheter 30 can be retracted through urethra 50. As can be seen, supporting plate 20 rests against the patient's labia L.

In a preferred aspect, catheter 30 can comprise a catheter positioning surface 31, such as an expandable balloon positioned between the patient's distal urethra DU and external meatus EM to engage soft tissues of urethra 50 so as to inhibit movement of catheter 30 within urethra 50 when the patent coughs. Alternatively, the outer surface of catheter 30 can be textured so as to gently grip against the sides of urethra 50, thereby holding catheter 30 in a fixed relative position to urethra 50. In a preferred aspect, a removable sheath is preferably received over the high friction surface such that the catheter can be conveniently inserted into the patient and positioned at a desired location. The sheath is then removed, such that the high friction surface of the catheter engages the walls of the urethra. Alternatively, fluid may be injected into the urethra, causing it to expand while the high friction surface catheter is inserted. Removal of the fluid surrounding the catheter will cause the urethra to collapse inwardly, such that the high friction surface of the catheter engages the walls of the urethra.

Figure 11:
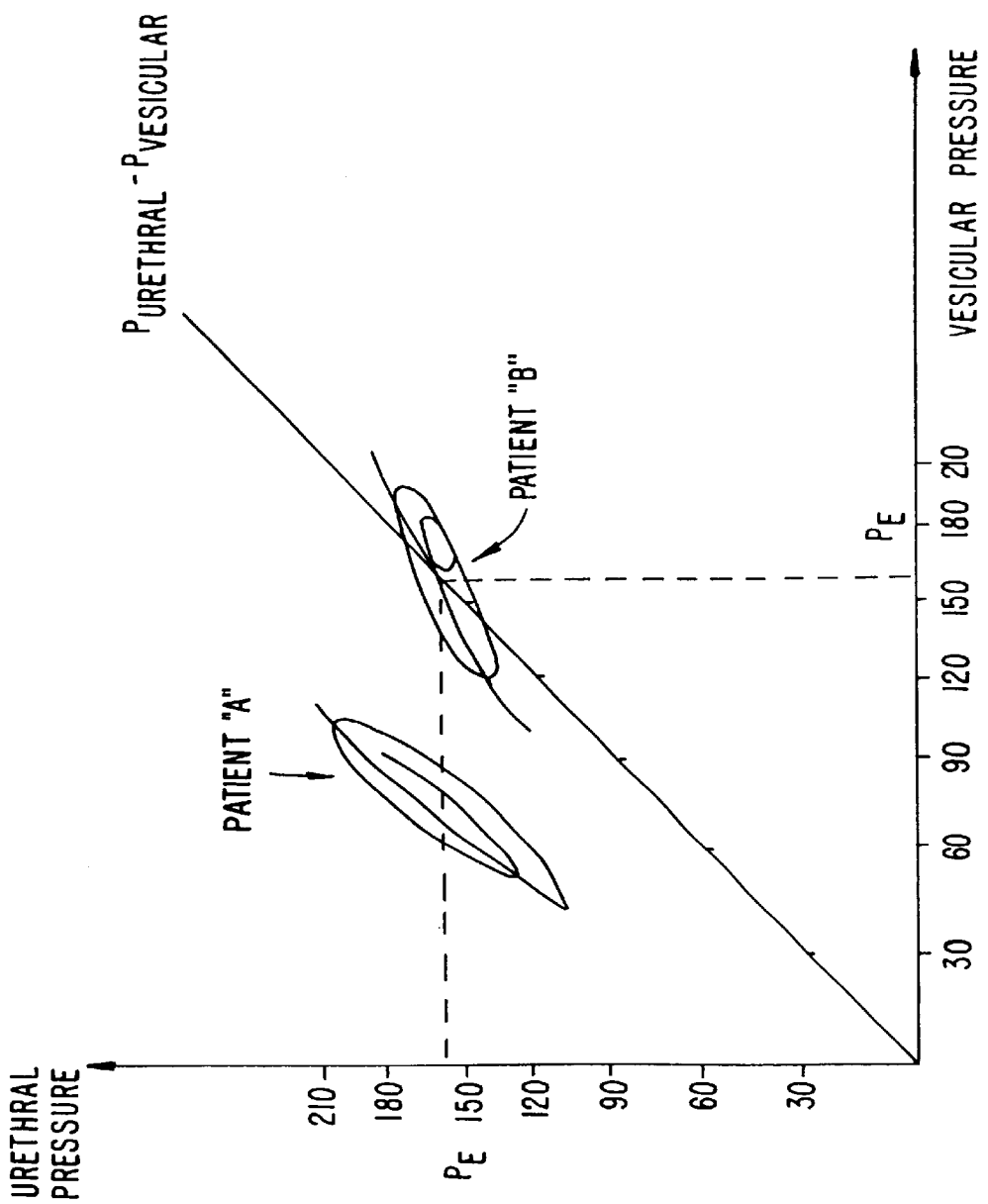
FIG. 11 is an illustration of a pressuregram showing the relationship between the vesicle pressure and the urethral pressure for two different patients at different abdominal pressures.

The pressures measured by pressure sensor 30 are received by computer system 62 and are displayed as a pressuregram on display terminal 64. FIG. 11 shows an exemplary pressuregram in which urethral pressure is plotted against vesicle pressure. The pressuregram shows the relationship between urethral and vesicle pressure for two different patients for different abdominal pressures caused by the patient coughing. Patient A's urethral pressure always exceeds her vesicle pressure, therefore patient A remains continent. For patient "B", however, her urethral pressure may be above or below her vesicle pressure, (as signified by her pressure data dropping below line $P_{urethral}$-$P_{vesicular}$), thus indicating incontinence at certain abdominal pressures.

What is claimed is:

1. A system for evaluating female urinary incontinence, comprising:

a catheter having at least one pressure sensor positioned thereon;

means for supporting the catheter to allow movement of the catheter in response to a pelvic pressure pulse, wherein the movement of the catheter tracks movement of the urethra of a patient during the pelvic pressure pulse; and a computer system in communication with the pressure sensor of the catheter, the computer system being adapted to generate a pressuregram of the relationship between urethral pressure and vesicle pressure in response to changes in pelvic pressure during the pelvic pressure pulse.

2. The system of claim 1, wherein the pressure sensing catheter comprises:

a catheter positioning surface positioned to engage soft tissues of the urethra so as to inhibit movement of the catheter within the urethra.

3. The system of claim 2, wherein the catheter positioning surface comprises:

a high friction surface of the catheter for engaging the surrounding urethra.

4. The system of claim 3, further comprising:

a removable sheath positioned over the high friction surface of the catheter.

5. The system of claim 1, wherein the pressure sensing catheter comprises:

a balloon positioned to engage soft tissues of the urethra so as to inhibit movement of the catheter within the urethra when the balloon is inflated.

6. A system for evaluating female urinary incontinence, comprising:

a catheter having at least one pressure sensor positioned thereon;

means for supporting the catheter to allow movement of the catheter in response to a pelvic pressure pulse, wherein the movement of the catheter tracks movement of the urethra of a patient during the pelvic pressure pulse; and a computer system in communication with the pressure sensor of the catheter, the computer system being adapted to generate a pressuregram of the relationship between urethral pressure and vesicle pressure in response to changes in pelvic pressure as the pressure sensor on the catheter is moved through the urethra of a patient.

7. The system of claim 1 or 6, further comprising:

a catheter retraction device for withdrawing the catheter to selectively position a pressure sensor on the catheter at each of proximal, mid and distal positions along the urethra.

8. The system of claim 6, further comprising:

a display terminal adapted to display the pressuregram.

9. A system for evaluating female urinary incontinence, comprising:

a catheter having a proximal end and a distal end, the distal end of the catheter insertable distally into a urethra of a patient so that the urethra surrounds the catheter;

a urethra engaging surface disposed on the catheter, the urethra engaging surface exposed to engage the surrounding urethra, engagement between the urethra engaging surface of the catheter and the urethra sufficient to effect movement of the catheter in response to movement of the urethra of a patient during a pelvic pressure pulse;

a urethral pressure sensor generating signals indicating a pressure at a urethral pressure location along the urethra, the urethral pressure sensor coupled to the catheter so that the pressure location tracks the movement of the urethra during the pressure pulse;

a vesicle pressure sensor coupled to the catheter distally of the urethral pressure sensor; and a computer system in communication with the urethral and vesicle pressure sensors of the catheter, the computer system generating a pressuregram of the relationship between urethral pressure and vesicle pressure in response to changes in pelvic pressure during the pelvic pressure pulse.

10. The system of claim 9, wherein the urethral engaging surface comprises a high friction surface of the catheter for engaging the surrounding urethra.

11. The system of claim 10, further comprising a removable sheath removably positioned over the high friction surface of the catheter so as to allow automatic insertion and removal of the catheter from the urethra.

* * * * *